United States Patent [19]

Wild et al.

[11] 4,061,858

[45] Dec. 6, 1977

[54] PURIFYING ACRYLONITRILE FOR THE MANUFACTURE OF ACRYLONITRILE POLYMERS

[75] Inventors: Hans Wild, Frankenthal; Rudolf Jung, Worms; Adolf Echte, Ludwigshafen; Johann Zizlsperger, Schriesheim; Hermann Gausepohl, Mutterstadt, all of Germany

[73] Assignee: BASF Aktiengesellschaft, Ludwigshafen, Germany

[21] Appl. No.: 703,955

[22] Filed: July 9, 1976

[30] Foreign Application Priority Data

Aug. 1, 1975 Germany .............................. 2534399

[51] Int. Cl.$^2$ .......................... C08F 6/00; C08F 20/44; C07C 121/30

[52] U.S. Cl. .................................. 526/67; 260/465.9; 526/68; 526/77

[58] Field of Search ............................ 526/67, 68, 77; 260/465.9

[56] References Cited

U.S. PATENT DOCUMENTS

| 2,351,157 | 6/1944 | Semon ............................... 260/465.9 |
| 2,555,798 | 6/1951 | Kropa .................................... 526/77 |
| 3,257,445 | 6/1966 | Roelen et al. ..................... 260/465.9 |

Primary Examiner—Alan Holler
Attorney, Agent, or Firm—Keil, Thompson & Shurtleff

[57] ABSTRACT

Acrylonitrile or monomer mixtures containing acrylonitrile are purified by treating them with alkaline reacting compounds followed by distillation. The products are particularly suitable for the manufacture of acrylonitrile polymers showing improved color stability.

16 Claims, No Drawings

PURIFYING ACRYLONITRILE FOR THE MANUFACTURE OF ACRYLONITRILE POLYMERS

The present invention relates to a process for the purification of acrylonitrile for the manufacture of acrylonitrile polymers, wherein acrylonitrile, optionally together with other monomers and/or solvent, is treated with alkaline substances and then distilled.

It is well known that polymers of acrylonitrile, for example copolymers of styrene and acrylonitrile, show a ready tendency to discoloration under thermal stress such as occurs during injection molding. There are therefore frequent recommendations for the addition of stabilizers to the polymers. It has been found, however, that the effect of the stabilizers is not usually sufficient to prevent discolorations completely.

Before it is fed to the polymerization reactor, the acrylonitrile, optionally together with other monomers or solvents, is distilled in order to remove from the monomer or monomers any undesirable impurities which could effect discoloration. Such a method is used, in particular, in continuous processes for the manufacture of styrene/acrylonitrile copolymers in which major amounts of styrene are polymerized with acrylonitrile in the presence of aromatic solvents, for example ethylbenzene, and the resulting polymers are separated from excess monomers and solvents. The mixture of solvent and monomer obtained after separation of the polymer is distilled, replenished with fresh monomer and recycled to the polymerization reactor.

It is an object of the present invention to provide a process for the purification of monomeric acrylonitrile, optionally together with other monomers copolymerizable with acrylonitrile and/or solvents, which produces acrylonitrile or a mixture of acrylonitrile with other copolymerizable monomers and/or solvent from which polymers may be prepared which show a much lower tendency to discoloration during thermoplastic treatment than the polymers known hitherto.

In accordance with the invention, this object is achieved by treating acrylonitrile or mixtures of acrylonitrile and other copolymerizable monomers, optionally together with solvents, with alkaline reacting compounds followed by distillation.

Our process is particularly suitable for the purification of mixtures of acrylonitrile, styrene and aromatic solvents, e.g. ethylbenzene, such as are separated from the polymer in the continuous polymerization of styrene/acrylonitrile copolymers and then recycled to the polymerization vessel.

Alkaline-reacting compounds which may be used in the process of the invention are substances which react as an alkaline material, in particular, hydroxides of metals in groups I and II of the Periodic Table and also basic aluminum oxide and basic ion exchangers. Particularly suitable are basic anion exchangers containing amino groups as the active groups. Alkali metal and alkaline earth metal hydroxides may be used both in the solid form and in the form of aqueous solutions. For example, acrylonitrile or the mixture of acrylonitrile and other monomers and/or solvents may be purified with aqueous alkali metal hydroxide solutions by the countercurrent method. Alternatively, the acrylonitrile or mixture of monomers and solvent may be passed through a column which is packed with solid alkaline-reacting substances, for example calcium oxide or a basic anion exchanger. If use is made of solutions of alkali metal hydroxides or alkaline earth metal hydroxides, it has been found that solutions containing from 0.1 to 5% by weight of the alkali metal hydroxide or alkaline earth metal hydroxide are suitable. The process may be carried out continuously or batchwise.

In the case of batchwise operation, the process is usually carried out in two stages, the acrylonitrile or acrylonitrile-containing monomer mixture being treated with the alkaline-reacting compounds in the first stage and then distilled in the second stage. A particularly advantageous continuous mode of operation consists in feeding the solution of an alkali metal hydroxide or alkaline earth metal hydroxide to the middle of a column for distilling acrylonitrile or mixtures thereof with other monomers and solvents such as styrene and ethylbenzene, the purified monomers being withdrawn at the top of the column whilst the residues containing the alkali metal hydroxide solution or alkaline earth metal hydroxide solution are withdrawn at the bottom of the column. It has been found that the process of the invention is particularly suitable for the purification of monomer mixtures or monomeric acrylonitrile containing from 0.1 to 2.0% by weight of impurities.

The treatment of the monomeric acrylonitrile or mixtures of acrylonitrile with further copolymerizable monomers and/or solvent with the alkaline-reacting compounds may be carried out in a relatively broad temperature range. However, the temperatures selected should not be unduly high, in order to avoid polymerization of the monomers. Advantageously, room temperature is used, for example a temperature range of from 15° to 35° C, but the process is not restricted to this temperature range.

Distillation of the monomers or the said mixture is advantageously carried out immediately after treatment with the alkaline compounds or, in the case of the continuous process, simultaneously with said treatment. Although conventional processes for distilling acrylonitrile may be used, it is recommended that the acrylonitrile or mixtures of acrylonitrile and other polymerizable compounds be distilled under pressures of from 20 to 150 mm of Hg and at temperatures of from 15° to 90° C. Such methods are described, for example, in Ullmanns Encyklopadie der technischen Chemie (1961), vol. 2/1, pp. 56 et seq.

The acrylonitrile or mixtures of acrylonitrile with other monomers and/or solvents obtained in the process of the invention have been found to give polymers showing a much lower tendency to discoloration under thermal stress than polymers of monomers or monomer mixtures which have merely been distilled prior to polymerization.

In the following Examples the percentages are by weight.

EXAMPLE 1

Acrylonitrile, together with the other monomers and solvents, was melted in a pressure tube under nitrogen and then thermally polymerized for 4 hours at 120° C and then for another 4 hours at 160° C and finally annealed for 8 hours at 240° C. The discoloration occurring as a result of the annealing was assessed by comparison with a dichromate scale.

The numerical data (dichromate scale) listed in the Table below indicate the amount of potassium dichromate dissolved in water in ppm units which is required to give the same depth of shade as the annealed polymer.

The mixture tested was one of 21% of acrylonitrile, 50% of styrene and 29% of ethylbenzene. This mixture was shaken, in one test, with 4% sodium hydroxide solution at room temperature and, after separation, distilled at from 23° to 86° C (100 mm of Hg). A mixture of the same composition was purified in a column having a height of 50 cm and a diameter of 2 cm and packed with calcium hydroxide and was then distilled under the same conditions. The residence time of the mixture in the column was 8 minutes. For purposes of comparison, the mixture of monomers and solvent was distilled without pretreatment.

The results are listed in the Table below. The letters RS (recycle solvent) indicate a mixture of acrylonitrile, styrene and ethylbenzene.

TABLE I

| Purifying operation | Percentage content of monomer mixture of | | | |
|---|---|---|---|---|
| | $\diagdown C=O \diagup$ | —COOH | Peroxide (%) | Color coefficient of annealed polymer |
| RS, untreated | 0.030 | 0.001 | 0.0050 | reddish brown |
| RS, distilled only | 0.025 | 0.0005 | 0.0040 | >1,000 |
| 4% of NaOH followed by distillation | 0.008 | 0.0005 | 0.0015 | 200 |
| Ca(OH)$_2$ followed by distillation | 0.006 | 0.0005 | 0.0018 | 200 |

EXAMPLE 2

A highly impure mixture of 21% of acrylonitrile, 50% of styrene and 29% of ethylbenzene was mixed with a 0.1% aqueous KOH solution and thoroughly shaken. It was then distilled as described in Example 1, the results being given in Table II below.

TABLE 2

| Purifying operation | Percentage content of monomer mixture of | | |
|---|---|---|---|
| | $\diagdown C=O \diagup$ | peroxide | Color coefficient of annealed polymer |
| RS, untreated | 0.16 | 0.010 | reddish brown |
| RS, distilled | 0.14 | 0.008 | reddish brown |
| 0.1% KOH with simultaneous distillation | 0.01 | 0.003 | 200–500 |

We claim:

1. A process for the purification of monomeric acrylonitrile or an acrylonitrile-containing monomer mixture to be used in the manufacture of an acrylonitrile polymer, which process comprises treating said monomeric acrylonitrile or a mixture of acrylonitrile and another copolymerizable monomer with an alkaline-reacting compound, and then distilling under a pressure of from 20 to 150 mm of Hg and at a temperature of from 15 to 90° C.

2. A process as claimed in claim 1, wherein a monomer mixture of styrene and acrylonitrile is used.

3. A process as claimed in claim 2, wherein a mixture of acrylonitrile, styrene and an aromatic solvent is used as obtained by separation from the polymer in the continuous polymerization of a styrene/acrylonitrile copolymer and recycled to the polymerization.

4. A process as claimed in claim 1, wherein the alkaline-reacting compounds used are hydroxides of metals in groups I and II of the Periodic Table or basic aluminum oxide.

5. A process as claimed in claim 1, wherein the alkaline-reacting compound is a basic anion exchanger containing amino groups as the active groups.

6. A process as claimed in claim 4, using an alkali metal hydroxide or alkaline earth metal hydroxide as the alkaline-reacting compound in the solid state or in the form of an aqueous solution.

7. A process as claimed in claim 6, which is carried out continuously by feeding the solution of an alkali metal hydroxide or alkaline earth metal hydroxide to the middle of a column used for distilling acrylonitrile or mixtures thereof with other monomers and solvents, the purified monomers being withdrawn at the top of the column, whilst the residues are withdrawn at the bottom of the column together with the alkali metal hydroxide solution or alkaline earth metal hydroxide solution.

8. A process as claimed in claim 1, wherein the treatment with an alkaline-reacting compound is carried out at a temperature at which no appreciable polymerization of monomers occurs.

9. A process for the purification of a monomeric mixture containing styrene and acrylonitrile to be used in the manufacture of a styrene/acrylonitrile copolymer, which process comprises treating said monomeric mixture of styrene and acrylonitrile with an alkaline-reacting compound and then distilling the treated mixture.

10. A process as claimed in claim 9 wherein said monomeric mixture of styrene and acrylonitrile contains an aromatic solvent.

11. A process as claimed in claim 10 wherein the aromatic solvent is ethylbenzene.

12. A process as claimed in claim 11 wherein the distillation is carried out under a pressure of from 20 to 150 mm of Hg and at a temperature of from 15° to 90° C.

13. A process as claimed in claim 9 wherein the alkaline-reacting compound being used is selected from the class consisting of hydroxides of metals in Groups I and II of the Periodic Table, a basic aluminum oxide and a basic anion exchanger containing amino groups as the active groups.

14. A process as claimed in claim 13 using an alkali metal hydroxide or alkaline earth metal hydroxide as the alkaline-reacting compound in the solid state or in the form of an aqueous solution.

15. A process as claimed in claim 14, which is carried out continuously by feeding the solution of an alkali metal hydroxide or alkaline earth metal hydroxide to the middle of a column used for distilling acrylonitrile or mixtures thereof with other monomers and solvents, the purified monomers being withdrawn at the top of the column, whilst the residues are withdrawn at the bottom of the column together with the alkali metal hydroxide solution or alkaline earth metal hydroxide solution.

16. A process as claimed in claim 9 wherein the treatment with an alkaline-reacting compound is carried out at a temperature at which no appreciable polymerization of the monomers occurs.

* * * * *